United States Patent
Li et al.

(10) Patent No.: US 6,444,615 B1
(45) Date of Patent: Sep. 3, 2002

(54) HERBICIDAL IMIDAZOLIDINETRIONE AND THIOXO-IMIDAZOLIDINEDIONES

(75) Inventors: Bin Li; Ying Man; Zongjian Zhang, all of Liaoning (CN); Adam Chi-Tung Hsu, Landsdale, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/551,345

(22) Filed: Apr. 18, 2000

(51) Int. Cl.⁷ .................... A01N 43/84; A01N 43/86; C07D 413/04; C07D 417/04; C07D 487/04
(52) U.S. Cl. .................. 504/225; 504/222; 504/237; 504/238; 504/243; 504/248; 504/270; 504/273; 504/275; 504/282; 504/285; 504/100; 504/229; 504/225; 544/105; 544/152; 544/51; 544/92; 548/221; 548/466; 548/180; 548/361.1; 549/362; 549/434; 549/446
(58) Field of Search ................... 544/105, 152, 544/51, 92; 549/362, 434, 446; 548/361.1, 180, 466, 221; 504/100, 225, 229, 238, 243, 248, 237, 270, 273, 275, 282, 285

(56) References Cited

U.S. PATENT DOCUMENTS

| 2,895,817 A | 7/1959 | Luckenbaugh |
| 4,902,334 A | 2/1990 | Azuma et al. ............. 71/88 |

FOREIGN PATENT DOCUMENTS

| EP | 0003619 A | 8/1979 |
| EP | 0018585 A | 11/1980 |
| EP | 0353198 A | 1/1990 |
| GB | 1324884 A | 7/1973 |
| JP | 53018569 A | 2/1978 |
| WO | 9322289 | 11/1993 |

Primary Examiner—Richard L. Raymond
Assistant Examiner—Kahsay Habte
(74) Attorney, Agent, or Firm—Thomas D. Rogerson

(57) ABSTRACT

This invention relates to 1-substituted-phenyl-3-substituted-2-thioxo-4,5-imidazolidinediones and 2,4,5-imidazolidinetriones which have activity as herbicides, to compositions which contain these compounds and to methods of use of these compounds. In particular, the present invention pertains to 2-thioxo-4,5-imidazolidinediones or 2,4,5-imidazolidinetriones wherein a 2,4,5,6-tetrasubstituted phenyl ring is linked to the heterocyclic ring.

9 Claims, No Drawings

HERBICIDAL IMIDAZOLIDINETRIONE AND THIOXO-IMIDAZOLIDINEDIONES

This invention relates to 1-substituted-phenyl-3-substituted-2-thioxo-4,5-imidazolidinediones and 2,4,5-imidazolidinetriones which have activity as herbicides, to compositions which contain these compounds and to methods of use of these compounds. In particular, the present invention pertains to 2-thioxo-4,5-imidazolidinediones or 2,4,5-imidazolidinetriones wherein a substituted phenyl ring is linked to the heterocyclic ring.

Certain 1-substituted phenyl-2-thioxo-4,5-imidazolidinediones and 2,4,5-imidazolidinetriones are known aldose reductase inhibitors (see U.S. Pat. No. 4,985,453), agricultural herbicides (see U.S. Pat. Nos. 2,895,817, 3,418,334, and 4,283,547), agricultural fungicides (see Japanese Patent disclosure 53018569), and agricultural insecticides (see International Patent Application No. WO 93/22289 A1). However, there is still a need for herbicidal compounds which have superior efficacy over those already known in the art.

We have discovered that certain compounds of this invention are surprisingly effective as pre-emergent and post-emergent herbicides. These compounds are represented by formula I

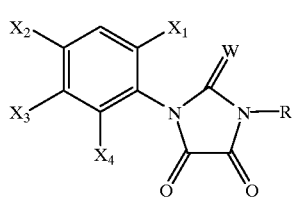

I wherein

R is hydrogen, $(C_1-C_8)$alkyl, $(C_3-C_6)$cycloalkyl, $(C_2-C_6)$alkenyl, $(C_3-C_6)$alkynyl, $(C_1-C_4)$alkoxy$(C_1-C_4)$alkyl, $(C_3-C_6)$cycloalkoxy$(C_1-C_4)$alkyl, $(C_2-C_6)$alkenyloxy$(C_1-C_4)$alkyl, $(C_3-C_6)$alkynyloxy$(C_1-C_4)$alkyl, $(C_1-C_{12})$alkylcarbonyl, $(C_1-C_4)$alkoxycarbonyl, $(C_2-C_6)$alkenyloxycarbonyl, cyano, dialkylamino, or $(C_1-C_6)$alkylsulfonyl;

$X_1$ is hydrogen or halo;

$X_2$ is halo, cyano, or nitro;

$X_4$ is hydrogen or halo;

$X_3$ is $(C_1-C_8)$haloalkyl, $(C_1-C_8)$alkoxy, $(C_3-C_6)$cycloalkoxy, $(C_2-C_6)$alkenyloxy, $(C_3-C_6)$alkynyloxy, $(C_1-C_{12})$alkylcarbonyl, $(C_1-C_4)$alkoxycarbonyl, $(C_2-C_6)$alkenyloxycarbonyl, $(C_3-C_6)$alkynyloxycarbonyl, $(C_1-C_8)$alkylsulfonylamino, $(C_1-C_8)$alkylsulfonylalkylamino, $(C_1-C_4)$alkoxycarbonylmethoxy, $(C_1-C_4)$alkoxycarbonylethoxy; or Q;

wherein Q is

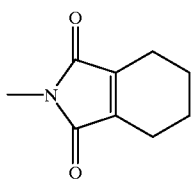

Q₁

-continued

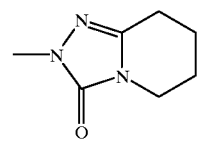

Q₂

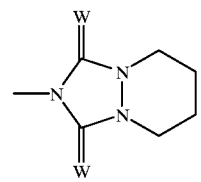

Q₃

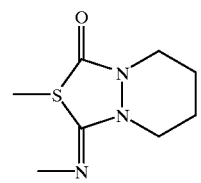

Q₄

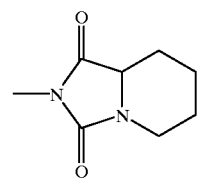

Q₅

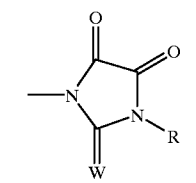

Q₆

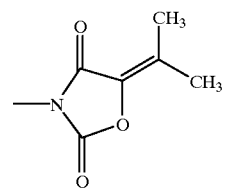

Q₇

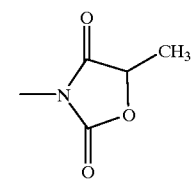

Q₈

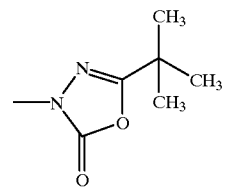

Q₉

-continued
Q10 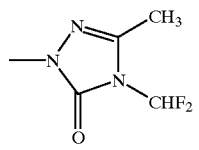
Q11 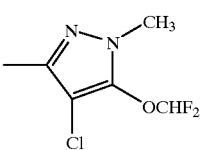
Q12 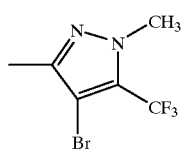
Q13 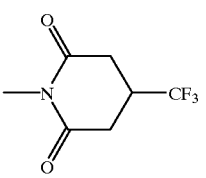
Q14 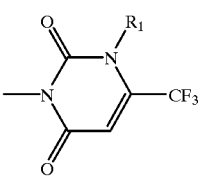
Q15 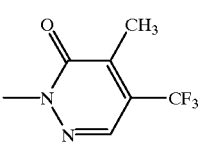
Q16 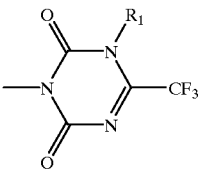
Q17 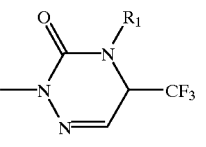
Q18 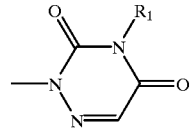
-continued
Q19 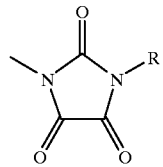
or
Q20 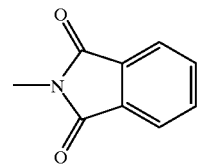
wherein $R_1$ is $NH_2$, OH, or $(C_1-C_4)$alkyl; and each W is independently oxygen or sulfur;
or, when $X_1$ is halo and $X_4$ is hydrogen, then $X_2$ and $X_3$ may form a 5- or 6-membered heterocyclic ring fused to the phenyl ring to form a bicyclic moiety of the formula:
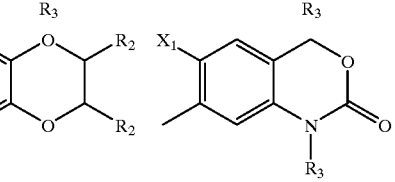
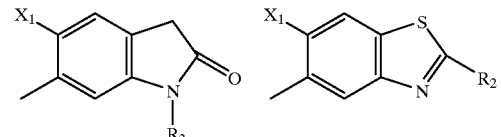
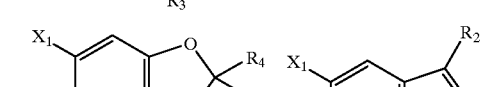
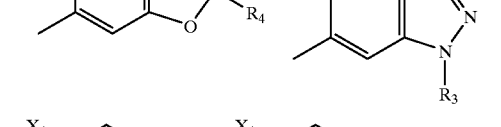
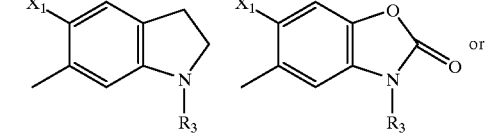
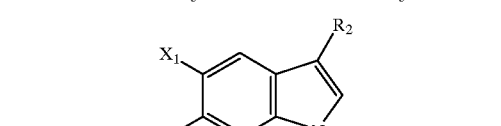
or
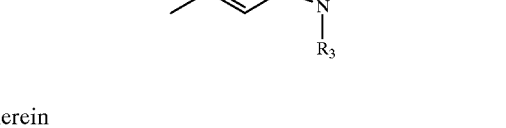
wherein
L is oxygen or sulfur;

$R_2$ is hydrogen or $(C_1-C_4)$alkyl;

$R_3$ is hydrogen; $(C_1-C_6)$alkyl, $(C_1-C_6)$haloalkyl, $(C_2-C_6)$alkenyl, $(C_3-C_6)$alkynyl; $(C_1-C_4)$alkoxyalkyl; $(C_2-C_6)$alkenyloxyalkyl; $(C_3-C_6)$alkynyloxyalkyl; cyanoalkyl; amino, or hydroxy; $R_4$ is hydrogen, $(C_1-C_3)$alkyl, or fluorine;

or when $X_1$ and $X_2$ are halo, then $X_3$ and $X_4$ form a 5- or 6-membered heterocyclic ring fused to the phenyl ring to which they are attached to form a bicyclic moiety having the structure

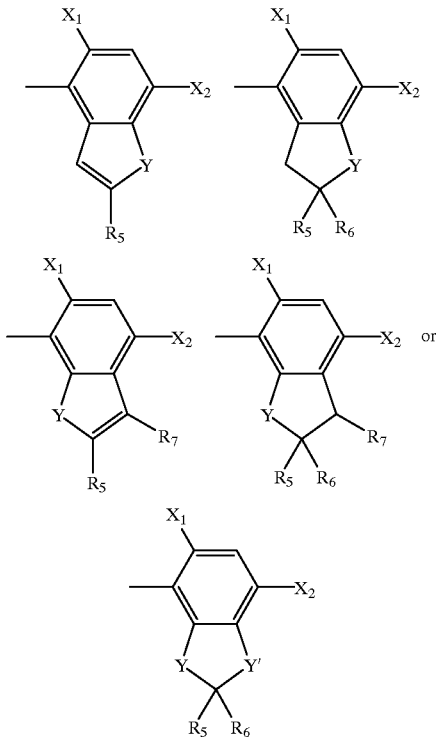

wherein
Y is oxygen, sulfur or —$NR_6$ wherein $R_6$ is hydrogen, $(C_1-C_6)$alkyl, $(C_3-C_5)$alkenyl or $(C_3-C_6)$alkynyl;

Y' is oxygen, sulfur, —$NR_6$, or —CO;

$R_5$ is hydrogen, halo, $(C_1-C_6)$alkyl, $(C_3-C_6)$cycloalkyl, $(C_2-C_6)$alkenyl, or $(C_3-C_6)$alkynyl, $(C_1-C_6)$haloalkyl, $(C_1-C_6)$alkoxy, cyano, $(C_1-C_6)$ hydroxyalkyl, —$CO_2R_8$, a formyl group, an acyl group, $(C_1-C_6)$alkylthio, $(C_1-C_6)$alkylsulfinyl, $(C_1-C_6)$alkylsulfonyl, $(C_1-C_6)$haloalkylthio, $(C_1-C_6)$haloalkylsulfinyl, $(C_1-C_6)$haloalkylsulfonyl, or a carboxyl group;

$R_6$ is hydrogen, $(C_1-C_6)$alkyl, $(C_3-C_6)$alkenyl, or $(C_3-C_6)$alkynyl;

$R_7$ is hydrogen, halo, $(C_1-C_6)$alkyl, $(C_1-C_6)$haloalkyl, an acyl group, or a nitro;

and agronomically acceptable salts thereof.

The term "alkyl" includes both branched and straight chain alkyl groups such as, for example, methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl and the like. The term "cycloalkyl" refers to a cyclic aliphatic ring structure such as cyclopropane, cyclobutane, cyclopentane, cyclohexane, cycloheptane, cyclooctane and the like. The term "haloalkyl" refers to an alkyl group substituted with one or more halo groups. The term "halo" refers to fluoro, chloro, bromo or iodo.

The term "alkylsulfonylalkyl" refers to an alkyl group substituted with an alkylsulfonyl (alkyl-$SO_2$) group, for example methylsulfonylmethyl. The term "alkylsulfinylalkyl" refers to an alkyl group substituted with an alkylsulfinyl (alkyl-SO) group, for example methylsulfinylmethyl.

The term "alkenyl" refers to an ethylenically unsaturated hydrocarbon group, straight or branched, having 1 or 2 ethylenic bonds. The term "haloalkenyl" refers to an alkenyl group substituted with one or more halo groups. The term "alkynyl" refers to an unsaturated hydrocarbon group, straight or branched, having 1 or 2 acetylenic bonds. The term "alkoxy" includes both branched and straight chain alkyl groups attached to a terminal oxygen atom such as, for example, methoxy, ethoxy, n-propoxy, isopropoxy, tert-butoxy and the like. The term "haloalkoxy" refers to an alkoxy group substituted with one or more halo groups.

The term "alkylthio" includes both branched and straight chain alkyl groups attached to a terminal sulfur atom. The term "haloalkylthio" refers to an alkylthio group substituted with one or more halo groups.

Agronomically acceptable salts may be formed by complexation of the compounds of the current invention with metal salts such as zinc chloride or iron chloride.

For purposes of this invention, unless otherwise indicated, all percentages, parts, and ratios are by weight and all ranges are inclusive and combinable.

Preferred compounds are compounds of formula I, wherein W is oxygen or sulfur; R is, $(C_1-C_6)$alkyl, $(C_1-C_4)$haloalkyl, $(C_4-C_6)$cycloalkyl, $(C_2-C_5)$alkenyl, $(C_3-C_6)$alkynyl, $(C_1-C_3)$alkoxyalkyl, $(C_4-C_6)$cycloalkoxyalkyl, $(C_2-C_5)$alkenyloxyalkyl, $(C_3-C_6)$alkynyloxyalkyl; $X_1$ is fluoro; $X_2$ is halo; $X_4$ is hydrogen or halo; $X_3$ is $(C_1-C_4)$alkoxy, $(C_3-C_6)$cycloalkoxy, $(C_2-C_6)$alkenyloxy, $(C_3-C_6)$alkynyloxy, $(C_1-C_4)$alkoxycarbonyl, $(C_2-C_6)$alkenyloxycarbonyl, $(C_3-C_6)$alkynyloxycarbonyl, $(C_1-C_6)$alkylsulfonylamino, $(C_1-C_4)$alkylsulfonylalkylamino, $(C_1-C_4)$alkoxycarbonylmethoxy, or $(C_1-C_3)$alkoxycarbonylethoxy; or when $X_1$ is fluoro and $X_4$ is hydrogen, then $X_2$ and $X_3$ form a 5- or 6 membered heterocyclic ring fused to the phenyl ring structure to form the bicyclic moiety wherein L is oxygen; $R_2$ is hydrogen or alkyl; $R_3$ is alkyl, haloalkyl, alkenyl, alkynyl; alkoxyalkyl; alkenyloxyalkyl; alkynyloxyalkyl; cyanoalkyl; amino, or hydroxy; and $R_4$ is hydrogen, $(C_1-C_3)$alkyl, or fluorine; and agronomically acceptable salts thereof.

More preferred compounds are compounds of Formula II

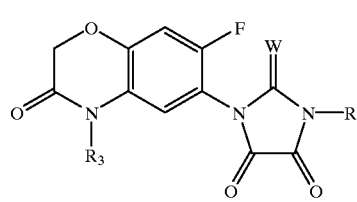

II wherein: W is oxygen or sulfur; R is $(C_1-C_3)$alkyl, $(C_1-C_3)$haloalkyl, $(C_5-C_6)$cycloalkyl, $(C_2-C_5)$alkenyl, $(C_3-C_6)$alkynyl; $R_3$ is $(C_1-C_3)$alkyl, $(C_1-C_3)$haloalkyl, $(C_2-C_5)$alkenyl, $(C_3-C_6)$alkynyl, $(C_1-C_3)$alkoxyalky, $(C_2-C_5)$alkenyloxyalkyl, $(C_3-C_6)$alkynyloxyalkyl; cyanoalkyl; and agronomically acceptable salts thereof.

The compounds of Formula I of the present invention can be prepared by the following processes:

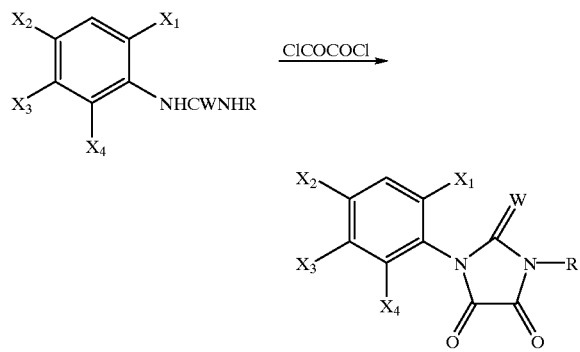

Substituted phenylureas (W=O) or thioureas (W=S) are reacted with oxalyl chloride in a solvent inert under the reaction conditions, e.g., chloroform, dichloromethane, carbon tetrachloride, hexane, benzene, toluene, ethyl acetate, DMF, tetrahydrofuran or dioxane to give compounds of Formula I, optionally in the presence of the bases such as $Et_3N$, pyridine, NaOH, KOH, $Na_2CO_3$, $K_2CO_3$, $NaHCO_3$ at a temperature from —40° C. to the boiling point of the solvent for 3 minutes to 48 hours.

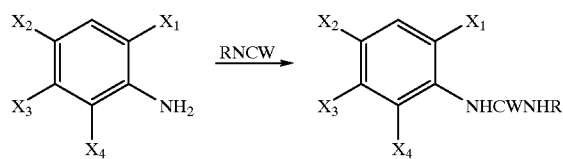

Substituted phenylanilines are reacted with isocyanates (W=O) or isothiocyanates (W=S), which are commercially available or can be prepared by known methods, in a solvent inert under the reaction conditions, e.g. chloroform, dichloromethane, carbon tetrachloride, hexane, benzene, toluene, ethyl acetate, DMF, tetrahydrofuran, alcohols, or dioxane to give phenylureas or phenylthioureas, optionally in the presence of the bases such as $Et_3N$ or pyridine as catalyst at a temperature from —40° C. to the boiling point of the solvent for 3 minutes to 48 hours.

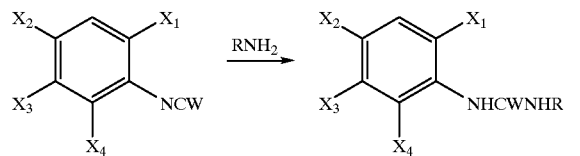

Substituted phenylisocyanates (W=O) or isothiocyanates (W=S), which are commercially available or can be prepared by known methods, are reacted with amines or anilines in a solvent inert under the reaction conditions, e.g., chloroform, dichloromethane, carbon tetrachloride, hexane, benzene, toluene, ethyl acetate, DMF, tetrahydrofuran or dioxane to produce phenylureas or phenylthioureas, optionally in the presence of the bases such as $Et_3N$ or pyridine as catalyst at a temperature from —40° C. to the boiling point of the solvent for 3 minutes to 48 hours. All amines or anilines are commercially available or can be prepared by known methods.

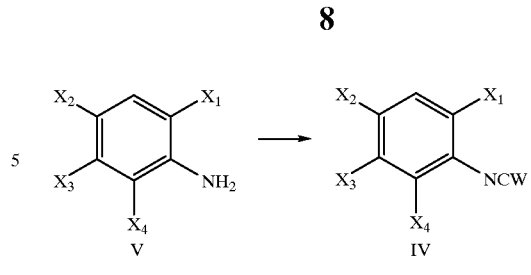

Substituted anilines are reacted with phosgene, diphosgene, triphosgene or oxalyl chloride in a solvent inert under the reaction conditions, e.g., chloroform, dichloromethane, carbon tetrachloride, hexane, benzene, toluene, ethyl acetate, DMF, tetrahydrofuran or dioxane to prepare phenyisocyanates or phenylisothiocyanates optionally in the presence of the bases such as $Et_3N$ or pyridine as catalyst at a temperature from —40° C. to the boiling point of the solvent for 3 minutes to 48 hours (c.f.*Chemistry and Technology of Isocyanates*: author: Henry Ulrich, Publisher: John Willy & Sons, page 1–192).

Anilines may be obtained from the nitro substituted benzene (made by known methods such as those described in European Patent Application No. 0 083 055 A2) by reacting with hydrogen or reductive metals such as iron, zinc, and titanium etc. in compatible solvents, such as chloroform, dichloromethane, carbon tetrachloride, hexane, benzene, toluene, DMF, tetrahydrofuran, dioxane, acetone, methyl ethyl ketone, ethanol or combined with an inorganic acid such as hydrochloric acid, at a temperature from —40° C. to the boiling point of the solvent for 3 minutes to 48 hours.

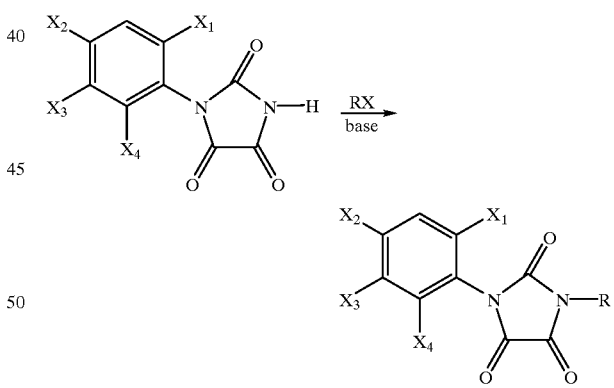

Alternatively, compounds of Formula I may be prepared by reacting compounds of Formula I-1 with an alkyl halide or alkyl sulfonylester in a solvent inert under the reaction conditions, e.g., chloroform, dichloromethane, carbon tetrachloride, hexane, benzene, toluene, ethyl acetate, acetone, DMF, tetrahydrofuran or dioxane, optionally in the presence of bases such as $Et_3N$, pyridine NaOH, KOH, $Na_2CO_3$, $K_2CO_3$, $NaHCO_3$ or sodium hydride at a temperature from —40° C. to the boiling point of the solvent for 3 minutes to 48 hours.

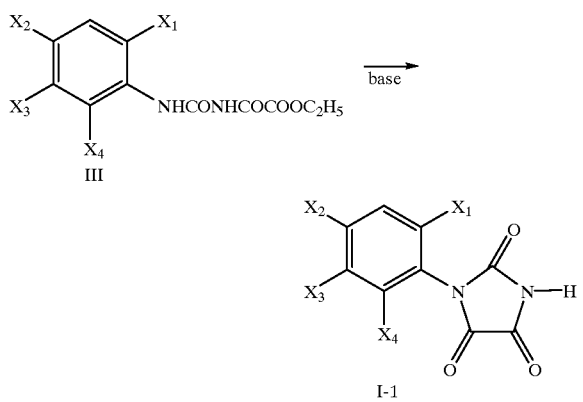

III

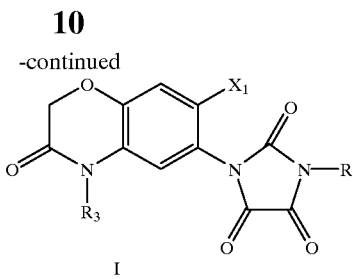

I

Compounds of Formula I-1 may be prepared by reacting compounds of Formula III with a base such as Et$_3$N, pyridine NaOH, KOH, Na$_2$CO$_3$ or K$_2$CO$_3$, in a solvent inert under appropriate reaction conditions, e.g., chloroform, dichloromethane, carbon tetrachloride, hexane, benzene, toluene, ethyl acetate, acetone, DMF, tetrahydrofuran or dioxane, at a temperature from —40° C. to the boiling point of the solvent for 3 minutes to 48 hours.

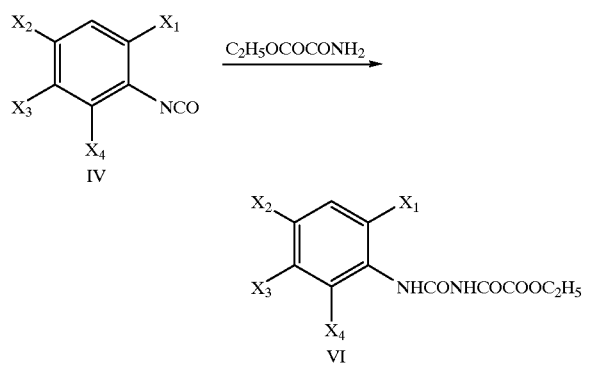

IV

VI

Compounds of Formula VI, in turn, can be prepared by reacting compounds of Formula IV, which can be prepared as shown in equation 4, or are commercially available, with ethyl oxamate, which is commercially available, in a solvent inert under the reaction conditions, e.g., chloroform, dichloromethane, carbon tetrachloride, hexane, benzene, toluene, ethyl acetate, DMF, tetrahydrofuran or dioxane, optionally in the presence of the bases such as Et$_3$N or pyridine as catalyst at a temperature from —40° C. to the boiling point of the solvent for 3 minutes to 48 hours.

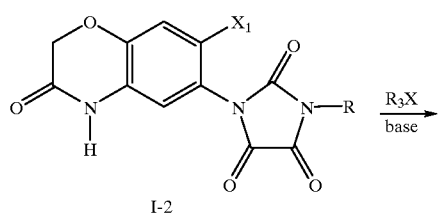

I-2

Certain compounds of the Formula I may be obtained by reacting compounds of Formula I-2, which can be prepared according to equation 1) with alkyl halide or alkyl sulfonylesters in a solvent inert under the reaction conditions, e.g., chloroform, dichloromethane, carbon tetrachloride, hexane, benzene, toluene, ethyl acetate, acetone, DMF, tetrahydrofuran or dioxane, optionally in the presence of the bases such as Et$_3$N, pyridine NaOH, KOH, Na$_2$CO$_3$, K$_2$CO$_3$, NaHCO$_3$ or sodium hydride at a temperature from —40° C. to the boiling point of the solvent for 3 minutes to 48 hours. Alkyl halide or alkyl sulfonylesters are commercially available or can be prepared by known methods.

Examples of compounds of the Formula I, prepared according to the above general methods, are listed in Tables 1 and 2. The preparation of several specific examples in this invention is described below in more detail.

EXAMPLES

1. Preparation Compound No. 5

A solution of 2-fluoro-4-chloro-5-cyclopentyloxyaniline (1.0 g, 5 mmol) in toluene (50 mL) was added dropwise to a solution of oxalyl chloride (2.0 g, 10 mmol) in toluene (20 mL) with stirring. The reaction mixture was stirred at room temperature for 1 hour and then heated to reflux for 4 hours until HCl evolution ceased. The mixture was cooled down to room temperature and the solvents were removed at reduced pressure to give 1.1 g of 2-fluoro-4-chloro-5-cylcopentyloxyphenyl isocyanate as an oily product. This was used in the next step without further purification.

The above product (0.3 g) was added into a solution of ammonium hydroxide (1 mL, excess) in CH$_2$Cl$_2$ (20 mL) with stirring. The solution was stirred at room temperature for 1 hour. The mixture was cooled to room temperature and the solvents were removed at reduced pressure to give 0.3 g of N-2-fluoro-4-chloro-5-cylcopentyloxyphenyl urea as a solid. Mp>248° C.

The above product (0.3 g) was added into a solution of oxalyl chloride (0.6 g mL, excess) in CH$_2$Cl$_2$ (20 mL) with stirring. The reaction solution was heated to reflux for 2 hours. The mixture was cooled to room temperature and was diluted with CH$_2$Cl$_2$ (80 mL). The mixture was washed sequentially with saturated NaHCO3 and brine, and then dried over MgSO$_4$. The solvents were evaporated at reduced pressure to give 0.2 g (yield 92%) of 1-(2-fluoro-4-chloro-5-cyclopentyloxy)phenyl-2,4,5-imidazolidinetrione as a solid, mp>248° C.

Methoxymethyl chloride (0.070 g, 60% in mineral oil, 1.8 mmol) was added into a mixture of the above product (0.45 g, 1.5 mmol) and K$_2$CO$_3$ in acetone (15 mL) with stirring. The reaction mixture was stirred at room temperature overnight and then combined with EtOAc (100 mL), washed sequentially with water and brine and then dried over Na$_2$SO$_4$. The solvent was removed at reduced pressure to give 0.3 g (yield 60%) of 1-methoxymethyl-3-(2-fluoro-4-chloro-5-cyclopentyloxy)phenyl-2,4,5-imidazolidinetrione as a solid, mp 90–91° C.

2. Preparation of Compound No. 18

A solution of 2-fluoro-4-chloro-5-methoxycarbonylaniline (1.0 g, 5 mmol) in THF (10 mL) was added dropwist to a solution of diphosgene (2.0 g, 10 mmol) in toluene (20 mL) with stirring at room temperature. The reaction mixture was stirred at room temperature for one hour and then heated to reflux for 4 hours. The mixture was then cooled to room temperature and the solvents were evaporated under reduced pressure to give 1.1 g of 2-fluoro-4-chloro-5-methoxycarbonylphenyl isocyanate as a solid. This was used for the next step without further purification.

The above product (0.3 g) was added into a solution of isopropylamine (1 mL, excess) in $CH_2Cl_2$ (20 mL) with stirring. The solution was stirred at room temperature for 1 hour. The solvent and excess isopropylamine were evaporated under reduced pressure to give 0.3 g of N-2-fluoro-4-chloro-5-methoxy-carbonylphenyl-N'-isopropyl urea as a solid. This product was used in the following step without further purification.

The above product (0.3 g) was added to a solution of oxalyl chloride (0.6 g mL, excess) in $CH_2Cl_2$ (20 mL) with stirring. The reaction mixture was heated to reflux for 2 h. The mixture was cooled and was diluted with $CH_2Cl_2$ (80 mL) and washed sequentially with saturated $NaHCO_3$ and brine and then dried over $MgSO_4$. The crude product was obtained after removing the solvents by evaporation. The 1-(2-fluoro-4-chloro-5-methoxycarbonylphenyl)-3-isopropyl-2,4,5-imidazolidinetrione (0.2 g) was obtained as a solid after purification on a silica gel column by chromatography (EtOAc/hexane: 1:3); mp 106–108° C.

3. Preparation of Compound No. 26 n-Propyl isocyanate (1.0 g, 11.7 mmol) was added to a solution of 7-fluoro-6-amino-4-(2-propynyl)-2H-1,4-benzoxazin-3(4H)-one (0.20 g, 0.9 mmol) in dioxane (20 mL) with stirring. The reaction mixture was heated to 80° C. for 4 hours. More n-propyl isocyanate (0.43 g, 5 mmol) was added and the reaction mixture was maintained at 80° C. overnight. Then the solution was concentrated to dryness to afford N-n-propyl-N'-[7-fluoro-4-(2-propynyl)-2H-1,4-benzoxazin-3(4H)-one-6-yl]urea as a crude intermediate (1.1 g). This was used for the next step without further purification.

The above product (0.3 g) was added to a solution of oxalyl chloride (0.6 mL, excess) in $CH_2Cl_2$ (20 mL) with stirring. The reaction mixture was heated to reflux for 2 hours. The mixture was then cooled to room temperature and was combined with $CH_2Cl_2$ (80 mL). The solution was washed sequentially with saturated $NaHCO_3$ and brine and then dried over $MgSO_4$. Solvents were removed at the reduced pressure to give a residue. The above crude product was purified by silica gel column chromatography (EtOAc/hexane: 1:3) to give 0.2 g (yield 92%) of pure 1-n-propyl-3-[7-fluoro-4-(2-propynyl)-2ZH-1,4-benzoxazin-3(4H)-one-6-]-2,4,5-imidazlidinetrione as a solid; mp 191–192° C.

TABLE 1

Representative Compounds of the Formula

| No | W | $X_1$ | $X_2$ | $X_3$ | $X_4$ | R |
|---|---|---|---|---|---|---|
| C1 | O | F | F | F | H | $CH_3CH_2CH_2$ |
| 2 | O | F | Cl | cyclopentyloxy | H | H |
| 3 | O | F | Cl | cyclopentyloxy | H | $CH_3$ |
| 4 | O | F | Cl | cyclopentyloxy | H | $CH_3CH_2$ |
| 5 | O | F | Cl | cyclopentyloxy | H | $CH_3OCH_2$ |
| 6 | O | F | Cl | cyclopentyloxy | H | $ClCH_2CH_2$ |
| 7 | O | F | Cl | cyclopentyloxy | H | $BrCH_2CH_2$ |
| 8 | O | F | Cl | cyclopentyloxy | H | $CH_3CH_2CH_2$ |
| 9 | O | F | Cl | cyclopentyloxy | H | propargyl |
| 10 | O | F | Cl | cyclopentyloxy | H | $CH_3CH_2CH_2CH_2$ |
| 11 | O | F | Cl | cyclopentyloxy | H | $(CH_3)_3C$ |
| 12 | O | F | Cl | propargyloxy | H | $CH_3$ |
| 13 | O | F | Cl | propargyloxy | H | $CH_3CH_2$ |
| 14 | O | F | Cl | propargyloxy | H | $CH_3CH_2CH_2$ |
| 15 | O | F | Cl | allyloxy | H | $CH_3$ |
| 16 | O | F | Cl | allyloxy | H | $CH_3CH_2CH_2$ |
| 17 | O | F | Cl | $C_2H_5OCOCH_2O$ | H | $CH_3$ |
| 18 | O | F | Cl | $CH_3OCO$ | H | $(CH_3)_2CH$ |
| 19 | O | F | F | $NO_2$ | H | $CH_3CH_2$ |
| 20 | O | H | Cl | $Q_2$ | H | $C_2H_5OCOCH_2$ |
| 21 | O | H | Cl | $Q_{14}$ | H | $C_2H_5OCOCH_2$ |

C1 = Comparison example

TABLE 2

Representative Compounds of the Formula

| No | W | $R_1$ | R |
|---|---|---|---|
| 22 | O | propargyl | $CH_3$ |
| 23 | O | propargyl | $CH_3CH_2CH_2$ |
| 24 | O | propargyl | $CF_3CH_2$ |
| 25 | S | propargyl | $CH_3CH_2CH_2$ |
| 26 | S | allyl | $CH_3CH_2CH_2$ |
| 27 | S | Et | $CH_3CH_2CH_2$ |
| 28 | S | n-Butyl | $CH_3CH_2CH_2$ |
| 29 | S | $CH_3OCH_2$ | $CH_3CH_2$ |
| 30 | S | propargyl | $CH_3CH_2$ |

TABLE 3

Physical Data of Representative Compounds of the Formula

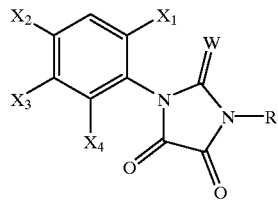

| Compound No | melting point (° C.) |
|---|---|
| C1 | 112–114 |
| 2 | 130–140 |
| 3 | 124–125 |
| 4 | 95–96 |
| 5 | 90–91 |
| 6 | 92–94 |
| 7 | 103–105 |
| 8 | 73–75 |
| 9 | 111–113 |
| 10 | 95–96 |
| 11 | 100–101 |
| 12 | 188–191 |
| 13 | 118–120 |
| 14 | 49–52 |
| 15 | 114–116 |
| 16 | 68–70 |
| 17 | 108–110 |
| 18 | 106–108 |
| 19 | 131–133 |
| 20 | 98–100 |
| 21 | 98–100 |

TABLE 4

Physical Data of Representative Compounds of the Formula

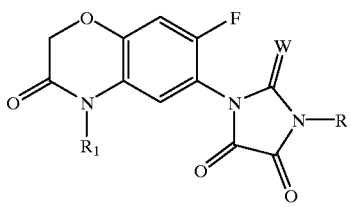

| Compound No | melting point (° C.) |
|---|---|
| 22 | 206–208 |
| 23 | 191–192 |
| 24 | 228–230 |
| 25 | 186–187 |
| 26 | 104–105 |
| 27 | 138–141 |
| 28 | Oil |
| 29 | 126–129 |
| 30 | 185–188 |

Compound No. 1H NMR (CDCl$_3$), TMS = 0 ppm

| 28 | 6.80 (d, 1H), 6.62 (d, 1H), 4.60 (s, 2H), 4.00–3.71 (m, 4H), 1.9–1.19 (m, 6H), 1.05–0.82 (m, 6H). |
|---|---|

Herbicide Activity

The compounds of Formula I are useful as an active ingredient for herbicides. When the compounds of Formula I are used as herbicides, the active ingredient can be used in a suitable formulation depending upon the particular purpose and application method. Usually, the active ingredient is diluted with an inert liquid or solid carrier, and used in the form of a formulation such as a dust, a wettable powder, an emulsifiable concentrate, aqueous or oil suspension, pellets, granules, etc., If desirable one may also add a surfactant and/or other addiyive. Furthermore, one of ordinary skill in the art will recognize that the conmpound of the present invention may be used in combination with an insecticide, a nematocide, a fungicide, other herbicides, a plant growth controlling agent, a fertilizer, etc.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined. Compositions and formulations according to the present invention may also include known Pesticidal compounds. This expands the spectrum of activity of the preparation and may give rise to synergism. Such adjuvants commonly used in the art can be found in *McCutcheon's Emulsifiers and Detergents, McCutcheon's Emulsifiers and Detergents/Functional Materials*, and *McCutcheon's Functional Materials* all published annually by McCutcheon Division of MC Publishing Company (New Jersey) and *Farm Chemicals Handbook* published by Meister Publishing Company (Ohio).

The formulations may contain from 0.1% to 99.9% by weight of active ingredient(s) and at least one of (a) 0.1% to 20% surfactant(s) and/or (b) 1% to 99.9% solid or liquid diluent(s).

If the compound of Formula I is formulated with an additional herbicide, the total concentration of active ingredient(s) in the compositions can vary within a wide range, depending on the active compound, the applications for which they are destined, the environmental conditions and the kind of formulation. The concentration of active ingredient(s) in the compositions is generally between 1% to 95%, preferably between 5% to 60%. In use, unwanted vegetation is controlled by applying to the vegetation, or to the soil wherein the unwanted vegetation grows, an herbicidally effective amount of a compound of Formula I or a composition comprising one or more compounds of Formula I and an agronomically acceptable carrier. The compounds and compositions of this invention can be diluted or applied as is to plant foliage and/or soil as aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the fungicide application rate, and the fungi to be controlled. The compositions can be mixed with fertilizers or fertilizing materials before their application.

The effective dose of the compounds of the present invention is usually within a range of from 10 g/ha to 3 kg/ha, preferably from 50 g/ha to 500 g/ha.

The following examples illustrate several aspects of this invention in detail:

Biological Testing

Listed below, a typical planting design for the test, consisting of four monocot weeds, four dicot weeds and one sedge weed.

| Common Name | Scientific Name |
|---|---|
| Grasses | |
| Barnyardgrass | *Echinochloa crusgalli* |
| Crabgrass (large) | *Digitaria sanguinalis* |
| Foxtail, (green) | *Setaria viridis* |
| Perennial Ryegrass | *Lolium perenne* |
| Sedges | |
| Nutsedge, (yellow) | *Cyperus esculentus* |
| Broad Leaf Weeds | |
| Hairy Beggarticks | *Bidens pilosa* |
| Nightshade, (black) | *Solanum nigrum* |
| Smartweed, (pale) | *Polygonum lapathifolium* |
| Velvetleaf | *Abutilon theophrasti* |

For each compound, evaluation tests were carried out according to the following procedures:

For preemergence tests, immediately after planting, the test compound was sprayed directly onto the soil surface. The flats or pots were placed in the greenhouse and then watered. For postemergence tests, seeds were allowed to germinate and grow for 10 to 21 days before application. The test plants were selected for uniformity, size and stage of development. The test plants were then treated with the test compound, returned to the greenhouse and watered. Untreated plants were used as a comparison.

The compound to be evaluated was dissolved in an appropriate solvent, usually acetone, or a formulation of the evaluated compounds as described above, was added to the water, and sprayed over the flats or pots using a carrier volume equivalent to 187 or 468 liters per hectare to give a rate of application in grams per hectare (g/ha). About two or four weeks after application of the test compounds, the state of the plant was observed. Each species was evaluated on a scale of 0–100 in which 0 equals no activity and 100 equals total control. Some of the test results are shown in Table 5

TABLE 5

Herbicidal Activity Test Results of Compounds of Formula I (pre-emergence/post-emergence) (1200 g/ha)

| # | BID | NS | SMT | VEL | BYG | CRB | FOX | NUT | RYE |
|---|---|---|---|---|---|---|---|---|---|
| C1 | 0/40 | 0/80 | 0/60 | 0/60 | 0/0 | 0/0 | 0/0 | 0/0 | 0/0 |
| 2 | 90/0 | 30/0 | 30/0 | 0/0 | 0/0 | 100/0 | 40/0 | 0/0 | 40/0 |
| 3 | 0/80 | 0/80 | 0/85 | 0/100 | 0/30 | 0/0 | 0/60 | 0/0 | 0/0 |
| 4 | 0/85 | 0/85 | 0/90 | 0/100 | 0/60 | 0/0 | 0/60 | 0/0 | 0/0 |
| 5 | 0/80 | 0/90 | 0/80 | 0/60 | 0/30 | 0/0 | 0/30 | 0/0 | 0/0 |
| 6 | 30/0 | 30/80 | 30/0 | 0/0 | 40/40 | 30/0 | 30/0 | 0/0 | 0/0 |
| 8 | 100/95 | 100/100 | 20/100 | 100/100 | 0/60 | 100/40 | 0/95 | 0/0 | 0/0 |
| 10 | 0/60 | 0/100 | 0/30 | 0/100 | 0/40 | 0/20 | 0/80 | 0/30 | 0/30 |
| 12 | 40/95 | 50/100 | 0/100 | 20/100 | 0/40 | 0/30 | 0/40 | 0/0 | 0/0 |
| 13 | 100/85 | 100/100 | 100/95 | 100/100 | 95/80 | 100/30 | 100/60 | 0/30 | 60/30 |
| 14 | 0/95 | 0/100 | 0/60 | 0/100 | 0/30 | 0/0 | 0/40 | 0/0 | 0/0 |
| 15 | 0/85 | 0/85 | 0/80 | 0/90 | 0/30 | 0/30 | 0/30 | 0/0 | 0/0 |
| 16 | 0/95 | 0/100 | 0/80 | 0/100 | 0/0 | 0/0 | 0/60 | 0/0 | 0/0 |
| 17 | 0/0 | 30/0 | 30/0 | 0/0 | 0/0 | 0/0 | 0/0 | 0/0 | 30/0 |
| 18 | 100/100 | 100/95 | 40/95 | 0/95 | 0/40 | 0/30 | 0/60 | 0/0 | 0/0 |
| 20 | *–/0 | –/40 | –/30 | –/60 | –/0 | –/0 | –/0 | –/0 | –/0 |
| 20 | 0/90 | 0/95 | 0/95 | 0/95 | 0/30 | 0/0 | 0/40 | 0/0 | 0/10 |
| 21 | –/0 | –/50 | –30 | –50 | –/0 | –/0 | –/0 | –/0 | –/0 |
| 22 | 95/80 | 95/100 | 85/90 | 40/100 | 40/60 | 100/40 | 100/80 | 0/60 | 0/30 |
| 23 | 100/95 | 100/100 | 100/95 | 100/100 | 100/60 | 100/0 | 100/60 | 95/40 | 90/0 |
| 24 | 0/40 | 0/60 | 0/40 | 0/60 | 0/0 | 0/0 | 0/0 | 0/0 | 0/0 |
| 25 | 100/100 | 100/100 | 100/100 | 100/100 | 100/30 | 100/30 | 100/60 | 80/40 | 85/0 |

*: – Means not tested.

We claim:
1. A compound of the formula;

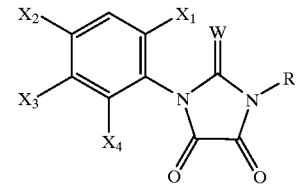

wherein
R is hydrogen, $(C_1-C_8)$alkyl, $(C_3-C_6)$cycloalkyl, $(C_2-C_6)$alkenyl, $(C_3-C_6)$alkynyl, $(C_1-C_4)$alkoxy$(C_1-C_4)$alkyl, $(C_3-C_6)$cycloalkoxy$(C_1-C_4)$alkyl, $C_2-C_6$)alkenyloxy $(C_1-C_4)$alkyl, $(C_3-C_6)$alkenyloxy$(C_1-C_4)$alkyl, $C_1-C_{12}$)alkylcaxbonyl, $(C_1-C_4)$alkoxycarbonyl, $(C_2-C_6)$alkenyloxycarbonyl, cyano, dialkylamino, or $(C_1-C_6)$alkylsulfonyl;;
$X_1$ is hydrogen or halo;
$X_2$ is halo, cyano, or nitro;

$X_3$ is $(C_1-C_8)$haloalkyl, $(C_1-C_8)$alkoxy, $(C_3-C_6)$cycloalkoxy, $(C_2-C_6)$alkenyloxy, $(C_3-C_6)$alkynyloxy, $(C_1-C_{12})$alkylcarbonyl, $(C_1-C_4)$alkoxycarbonyl, $(C_2-C_6)$alkenyloxycarbonyl, $(C_3-C_6)$alkyloxycarbonyl, $(C_1-C_8)$alkylsulfonylamino, $(C_1-C_8)$alkylsulfonylalkylamino, $(C_1-C_4)$alkoxycarbonylmethoxy, $(C_1-C_4)$alkoxycarbonylethoxy; or Q;

wherein Q is $Q_1$
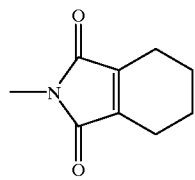

$Q_2$
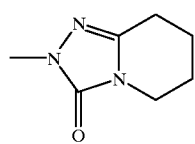

$Q_3$
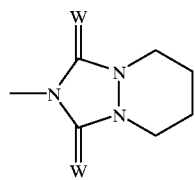

$Q_4$
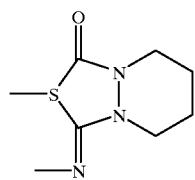

$Q_5$
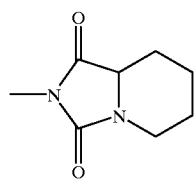

$Q_6$
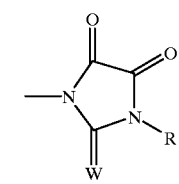

$Q_7$
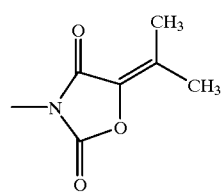

-continued $Q_8$
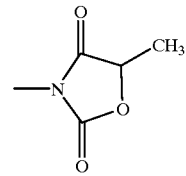

$Q_9$
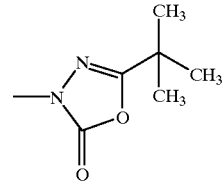

$Q_{10}$
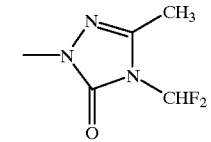

$Q_{11}$
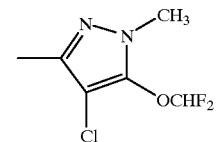

$Q_{12}$
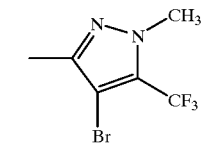

$Q_{13}$
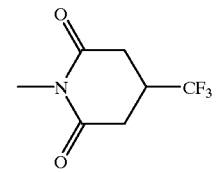

$Q_{14}$
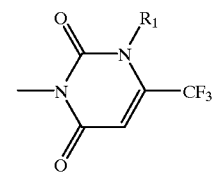

$Q_{15}$
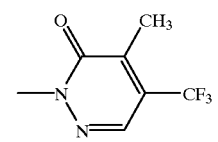

$Q_{16}$
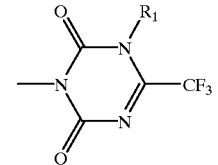

-continued

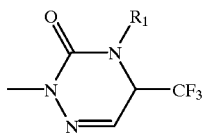

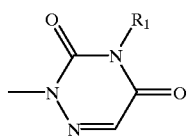

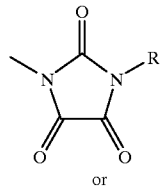

or

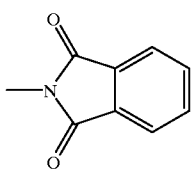

wherein $R_1$ is $NH_2$, OH, or $(C_1-C_4)$alkyl; and $X_4$ is hydrogen or halo;

each W is independently oxygen or sulfur;

or, when $X_1$ is halo and $X_4$ is hydrogen, then $X_2$ and $X_3$ may form a 5- or 6-membered heterocyclic ring fused to the phenyl ring to form a bicyclic moiety having the structure

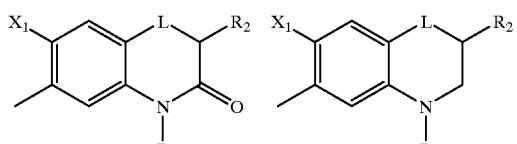

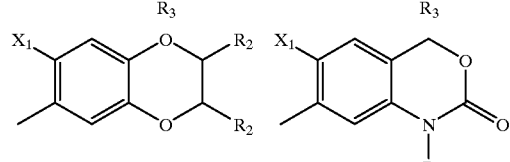

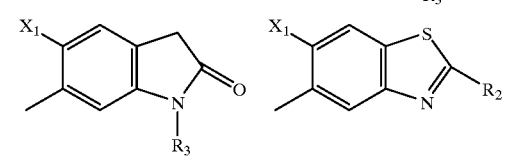

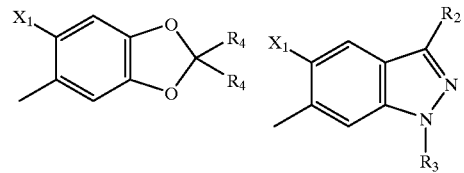

$Q_{17}$ $Q_{18}$ $Q_{19}$ $Q_{20}$

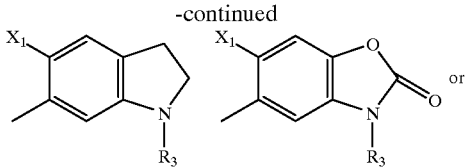 or

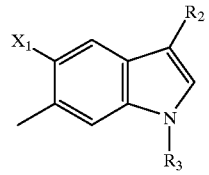

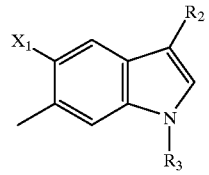

wherein
L is oxygen or sulfur;
$R_2$ is hydrogen or $(C_1-C_4)$alkyl;
$R_3$ is hydrogen; $(C_1-C_6)$alkyl, $(C_1-C_6)$haloalkyl, $(C_2-C_6)$alkenyl, $(C_3-C_6)$alkynyl; $(C_1-C_4)$alkoxyalkyl; $(C_2-C_6)$alkenyloxyalkyl; $(C_3-C_6)$alkynyloxyalkyl; cyanoalkyl; amino, or hydroxy; and
$R_4$ is hydrogen, $(C_1-C_3)$alkyl or fluorine;
or, when $X_1$ and $X_2$ are halo, then $X_3$ and $X_4$ form a 5- or 6-membered heterocyclic ring fused to the phenyl ring to which they are attached to form a bicyclic moiety having the structure

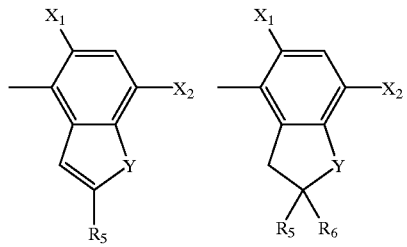

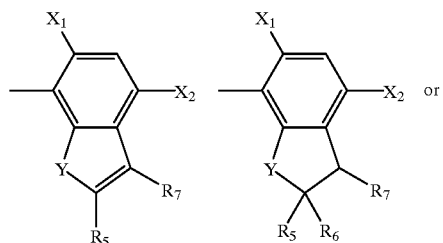

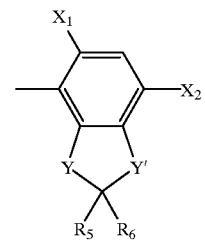

wherein
Y is oxygen, sulfur or —$NR_6$ wherein $R_6$ is hydrogen, $(C_1-C_6)$alkyl, $(C_3-C_5)$alkenyl or $(C_3-C_6)$alkynyl;
Y is oxygen, sulfur, —$NR_6$, or —CO;
$R_5$ is hydrogen, halo, $(C_1-C_6)$alkyl, $(C_3-C_6)$cycloalkyl, $(C_2-C_6)$alkenyl, or $(C_3-C_6)$alkynyl, $(C_1-C_6)$haloalkyl, $(C_1-C_6)$alkoxy, cyano, $(C_1-C_6)$ hydroxyalkyl, —$CO_2R_8$, a formyl group, an acyl group, $(C_1-C_6)$alkylthio, $(C_1-C_6)$alkylsulfinyl, $(C_1-C_6)$alkylsulfonyl, ($C_1$–$C_6$)haloalkylthio, ($C_1$–$C_6$)haloalkylsulfinyl, ($C_1$–$C_6$)haloalkysulfonyl, or a carboxyl group;

$R_6$ is hydrogen, ($C_1$–$C_6$)alkyl, ($C_3$–$C_6$)alkenyl, or ($C_3$–$C_6$)alkynyl;

$R_7$ is hydrogen, halo, ($C_1$–$C_6$)alkyl ($C_1$–$C_6$)haloalkyl, an acyl group, or a nitro;

and agronomically acceptable salts thereof.

2. The compound of claim 1, wherein R is, ($C_1$–$C_6$)alkyl, ($C_1$–$C_4$)haloalkyl, ($C_4$–$C_6$)cycloalkyl, ($C_2$–$C_5$)alkenyl, ($C_3$–$C_6$)alkynyl, ($C_1$–$C_3$)alkoxyalkyl, ($C_4$–$C_6$)cycloalkoxyalkyl, ($C_2$–$C_5$)alkenyloxyalkyl, ($C_3$–$C_6$)alkynyloxyalkyl.

3. The compound of claim 1, wherein $X_1$ is fluoro.

4. The compound of claim 1, wherein $X_2$ is halo.

5. The compound of claim 1, wherein:

$X_3$ is ($C_1$–$C_4$)alkoxy, ($C_3$–$C_6$)cycloalkoxy, ($C_2$–$C_6$)alkenyloxy, ($C_3$–$C_6$)alkynyloxy, ($C_1$–$C_4$)alkoxycarbonyl, ($C_2$–$C_6$)alkenyloxycarbonyl, ($C_3$–$C_6$)alkynyloxycarbonyl, ($C_1$–$C_6$)alkylsulfonylamino, ($C_1$–$C_4$)alkylsulfonylalkylamino, ($C_1$–$C_4$)alkoxycarbonylmethoxy, or ($C_1$–$C_3$)alkoxycarbonylethoxy; or when $X_1$ is fluoro and $X_4$ is hydrogen, then $X_2$ and $X_3$ form a 5- or 6-membered heterocyclic ring fused to the phenyl ring structure to form a bicyclic moiety wherein L is oxygen; $R_2$ is hydrogen or alkyl; $R_3$ is alkyl, haloalkyl, alkenyl, alkynyl; alkoxyalkyl; alkenyloxyalkyl; alkynyloxyalkyl; cyanoalkyl; amino, or hydroxy; and $R_4$ is hydrogen, ($C_1$–$C_3$)alkyl, or fluorine.

6. The compound of claim 1 wherein $X_4$ is hydrogen or halo.

7. The compound of claim 1, wherein $X_2$ and $X_3$ are joined to form a compound of the formula:

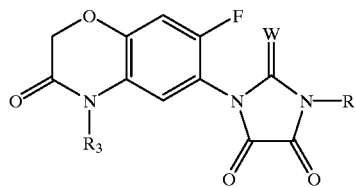

wherein:

R is ($C_1$–$C_3$)alkyl, ($C_1$–$C_3$)haloalkyl, ($C_5$–$C_6$)cycloalkyl, ($C_2$–$C_5$)alkenyl, or ($C_3$–$C_6$)alkynyl; and $R_3$ is ($C_1$–$C_3$)alkyl, ($C_1$–$C_3$)haloalkyl, ($C_2$–$C_5$)alkenyl, ($C_3$–$C_6$)alkynyl, ($C_1$–$C_3$)alkoxyalky, ($C_2$–$C_5$)alkenyloxyalkyl, ($C_3$–$C_6$)alkynyloxyalkyl; or cyanoalkyl.

8. A composition comprising one or more compounds of claim 1 and an agronomically acceptable carrier.

9. A method for controlling unwanted vegetation comprising applying to the vegetation, or to the soil wherein the unwanted vegetation grows, an herbicidally effective amount of one or more compounds of claim 1 or one or more compositions of claim 8.

* * * * *